United States Patent [19]

Kim et al.

[11] Patent Number: 5,739,105
[45] Date of Patent: Apr. 14, 1998

[54] CYCLOSPORIN CONTAINING COMPOSITION AND PROCESS FOR THE PREPARATION THEREOF

[75] Inventors: Hyun Soo Kim, Kwacheon-Si; Jae Yoon Choi, Ahnyang-Si; Hye Weon Lee, Ahnyang-Si; Young Keun Park, Ahnyang-Si; Sung Wook Choi, Seoul, all of Rep. of Korea

[73] Assignee: Yuhan Corporation, Seoul, Rep. of Korea

[21] Appl. No.: 732,377

[22] PCT Filed: May 19, 1995

[86] PCT No.: PCT/KR95/00059

§ 371 Date: Nov. 13, 1996

§ 102(e) Date: Nov. 13, 1996

[87] PCT Pub. No.: WO95/32726

PCT Pub. Date: Dec. 7, 1995

[30] Foreign Application Priority Data

Jun. 1, 1994 [KR] Rep. of Korea .................. 94-12288

[51] Int. Cl.$^6$ .................. A61K 38/00; A61K 38/13
[52] U.S. Cl. .................................. 514/11; 514/21
[58] Field of Search .................................. 514/11, 21

[56] References Cited

FOREIGN PATENT DOCUMENTS 0335627  4/1989  European Pat. Off. .

Primary Examiner—Cecilia J. Tsang
Assistant Examiner—P. Lynn Touzeku
Attorney, Agent, or Firm—Anderson, Kill & Olick, P.C.

[57] ABSTRACT

A composition comprising 1.0 to 40 wt. % of a cyclosporin A, 0.1 to 30 wt. % of an emulsifier and 5 to 80 wt. % of a porous dextrin, based on the total weight of the composition has a remarkably improved dissolution rate and superior bioavailability.

11 Claims, 1 Drawing Sheet

CYCLOSPORIN CONTAINING COMPOSITION AND PROCESS FOR THE PREPARATION THEREOF

This application is a 371 of PCT/KR95/00059, filed 19 May 1995.

FIELD OF THE INVENTION

The present invention relates to a composition comprising a cyclosporin, and to a process for the preparation thereof.

DESCRIPTION OF THE PRIOR ART

Cyclosporins, a group of cyclic polypeptides comprised of 11 amino acids having the structural formula (I), are useful as an immunosuppressive which suppresses allogenic transplant rejection which may occur in the transplantation of organs of animals including human beings.

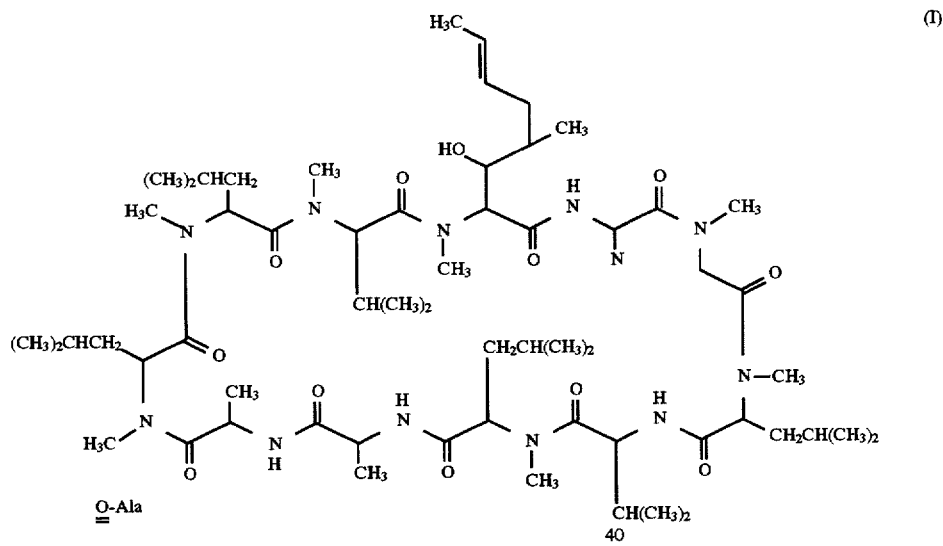

(I)

Cyclosporin A: $R=CH_2CH_3$;
Cyclosporin B: $R=CH_3$;
Cyclosporin C: $R=CH(OH)-CH_3$;
Cyclosporin D: $R=CH(CH_3)_2$; and
Cyclosporin G: $R=CH_2CH_2CH_3$.

In spite of their usefulness, however, pharmaceutical formulations containing cyclosporins have seen limited applications because of their extremely low solubility in water (20–30 µg/ml).

U.S. Pat. No. 4,388,307 describes pharmaceutical compositions containing cyclosporins (SANDIMMUN or SANDIMMUNE) in the form of a solution for injection or oral administration, or a soft capsule filled with the solution. The solution is prepared by dispersing a cyclosporin into a vegetable oil by using an ethoxylated castor oil (obtained from a reaction between natural or hydrogenated castor oil and ethylene oxide) or a transesterification product of a natural vegetable oil triglyceride and a polyalkylene polyol as an emulsifier, and ethanol as a solubilizing agent. However, the process has certain drawbacks. For example, when the oily composition is contacted with an aqueous solution in mouth or intestine, the drug component is often separated as a solid, thereby reducing its bioavailability to a level of, e.g., below 30%. Moreover, in case of a long period storage, cyclosporins tend to be crystallized as the ethanol content decreases by evaporation; and patients suffer from the unpleasant odor of the ethoxylated castor oil.

Accordingly, many attempts have been made in search for a cyclosporin containing formulation with improved stability and bioavailability. For example, Japanese Patent No. 89-38029 describes a method of dissolving a cyclosporin in an organic solvent with a surfactant and then drying the resultant; German Patent Nos. 295,765 and 295,766 offer a method of dissolving cyclosporins in ethanol with a surfactant and lyophilizing the resultant; PCT international publication No. WO 90-00389 discloses a method of solubilizing cyclosporins by using a liposome and lyophilizing the resultant; and German Patent No. 293,499 presents a method of dissolving cyclosporins in propylene glycol, suspending the solution with a polymeric polysaccharide, and solidifying the suspension with a solid carrier.

Even though the above processes may have achieved some success in improving the stability of the formulation through minimizing the ethanol content therein, they still suffer from various deficiencies. For example, the use of surfactants having a complicated composition is not practically suitable or desirable for preparing the formulation; liposome makes the whole process complicated and the reproducibility of particle size or inclusion rate is hard to control; and the use of a polymeric polysaccharide may turn the total volume of the formulation to be too bulky for administration. Further, the prior art methods still fail to produce cyclosporin containing compositions which have a satisfactory dissolution rate in an aqueous solution.

SUMMARY OF THE INVENTION

Accordingly, it is an object of the present invention to provide a cyclosporin containing composition having improved stability as well as a high dissolution rate and blood concentration of cyclosporin.

It is another object of the present invention to provide a process for the preparation of the inventive composition.

In accordance with one aspect of the present invention, there is provided a composition comprising 1.0 to 40 wt. % of a cyclosporin A, 0.1 to 30 wt. % of an emulsifier and 5 to 80 wt. % of a porous dextrin, based on the total weight of the composition.

In accordance with another aspect of the present invention, there is provided a process for preparing a cyclosporin containing composition comprising the steps of dissolving the cyclosporin A in ethanol with an emulsifier, adding a porous dextrin thereto to form a mixture, and drying the mixture.

DETAILED DESCRIPTION OF THE INVENTION

Figure 1:
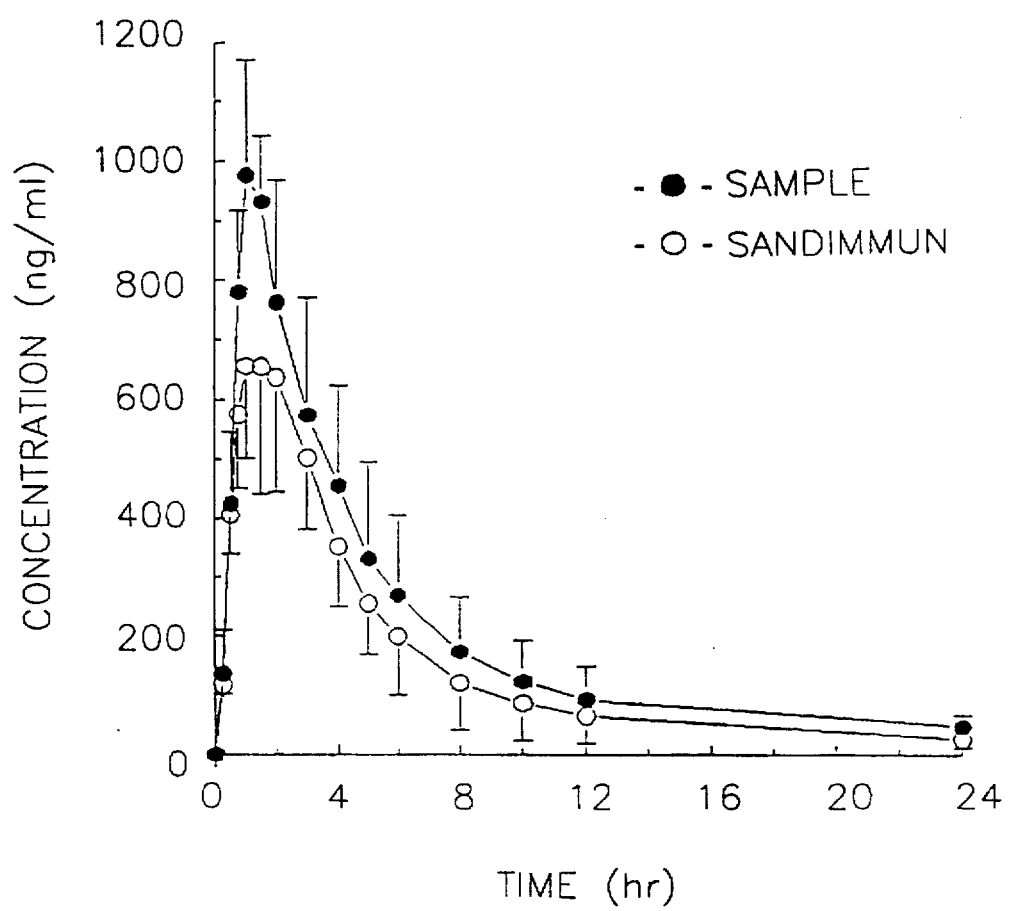
FIG. 1 shows the blood concentration of a cyclosporin of the composition of the present invention (●) and SANDIMMUN (○) in a time interval.

A porous dextrin, which may be advantageously used in the composition of the present invention, has a high porosity. It is soluble in water, but insoluble in ethanol. When a porous dextrin is added to an ethanolic solution containing a cyclosporin and an emulsifier, the solution is adsorbed into pores of the porous dextrin, to thereby disperse the cyclosporin and the emulsifier in the porous dextrin. In case that the mixture of the porous dextrin and the ethanolic solution containing the cyclosporin and the emulsifier is diluted with a large amount of water, it is microemulsified to form an emulsion, which applied to the case that the mixture is administered into the body having an aqueous environment. Such porous dextrin may be also added as an aqueous solution thereof to the ethanolic solution containing a cyclosporin and an emulsifier, then the mixture is microemulsifed by the action of the emulsifier to form a homogeneous solution. That is, the cyclosporin containing composition of the present invention shows microemulsification which increases the spreadibility of the drug and delays its crystallizing process in vivo, to thereby accelerate the dissolution of cyclosporin. Besides, the composition of the present invention can be formulated into a solid form which has an increased stability and a high dissolution rate.

The cyclosporin containing composition of the present invention may be prepared in accordance with the procedure described below in detail.

First, a cyclosporin A is dissolved in ethanol together with an emulsifier. As the emulsifier, various pharmaceutically acceptable surfactants, preferably, Tyloxapol, Poloxamer, Tween, Labrafil and Cremophor, may be used. The emulsifier may be employed in an amount ranging from 0.1 to 30 wt. %, preferably from 1 to 15 wt. %, based on the total weight of the composition. The amount of the cyclosporin A may range from 1.0 to 40 wt. %, preferably from 8 to 15 wt. %, based on the total weight of the composition. Ethanol may be used in sufficient amount to dissolve the cyclosporin A and emulsifier.

Then, a porous dextrin is added into the ethanolic solution containing the cyclosporin A and emulsifier, in an amount ranging from 5 to 80 wt. % based on the total weight of the composition. The porous dextrin may be added in the form of an aqueous solution thereof. The concentration of cyclosporin A in the aqueous solution ranges preferably from 20 to 50%(wt./wt.).

Then, the resultant mixture is dried to obtain a cyclosporin containing composition of the present invention, e.g., in the form of fine powder or granule. Drying may be carried out by using any conventional method, preferably spray drying or drying under a reduced pressure. For example, the composition of the present invention in the form of a fine powder may be prepared effectively by using an aqueous solution of the porous dextrin and then removing water and ethanol by spray drying.

On the other hand, the composition of the present invention in the form of a granule may be prepared by using a porous dextrin powder, and then drying it under a reduced pressure.

The cyclosporin containing composition of the present invention may be formulated in a conventional manner, if desired, with other pharmaceutical carriers, into a tablet or a capsule. The pharmaceutically acceptable carriers may include: a disintegrator such as starches, alginic acid, microcrystalline cellulose, etc.; a binding agent such as starch paste (from 10 to 80%), gelatin solution (from 10 to 20%), methylcellulose, ethylcellulose, carboxymethylcellulose, polyethyleneglycol 4000, polyethyleneglycol 6000, polyvinyl pyrolidone, etc.; a lubricant such as magnesium stearate, calcium stearate, stearic acid, etc.; and an excipient such as lactose, sugar, sodium chloride, calcium sulfate, calcium carbonate, mannitol, sorbitol, talc, mineral oil, etc.; and other pharmaceutically acceptable colorant, flavoring agent, sweetening agent, coating material and preservatives.

As described above, the cyclosporin containing composition of the present invention, when being administered into a body, may be microemulsified; and consequently, the spreadibility of the cyclosporin A increases, its crystallizing decreases in vivo, and the dissolution rate markedly increases. In addition, the composition of the present invention contains very little ethanol, and, therefore, is essentially free from the stability problem caused by ethanol evaporation. Besides, the composition of the present invention has the advantage in that it can be easily formulated into a solid form.

The composition of the present invention may preferably be administered orally. The therapeutically effective amounts of cyclosporin A to be administered are well-known, e.g., a daily dosage of from about 2 mg/kg to about 14-17.5 mg/kg.

The following Examples and Tests are intended to illustrate the present invention more specifically, without limiting the scope of the invention.

EXAMPLE 1

4 g of cyclosporin A (PINEFLOW, Matsutani Chemical Co.(Japan), specific volume: 8.5 cm$^3$/g) and 2 g of Poloxamer 407 were dissolved in 20 g of ethanol. A solution of 10 g of a porous dextrin in 40 g of purified water was added to the ethanolic solution, and the mixture was stirred for 10 minutes. The resultant was dried by spray dryer (inlet temperature: 105° C., outlet temperature: 75° C., air spraying pressure: 3 kg/cm$^2$) to obtain the composition of the present invention in powder form. The ethanol content in the powder was measured by high pressure liquid chromatography(HPLC.), and the result is shown in Table 1 below.

EXAMPLES 2-5

The procedure of Example 1 was repeated except that the amounts of the cyclosporin A, Poloxamer 407, ethanol, the porous dextrin and purified water were varied as shown in Table 2 to obtain the compositions of the present invention in powder formulations. Their ethanol content were measured and the results are shown in Table 1 below.

TABLE 1

| Composition | Ex. 1 | Ex. 2 | Ex. 3 | Ex. 4 | Ex. 5 |
| --- | --- | --- | --- | --- | --- |
| Cyclosporin A (g) | 4 | 6 | 8 | 8 | 8 |
| Poloxamer 407 (g) | 2 | 3 | 4 | 5 | 6 |
| Porous dextrin (g) | 10 | 10 | 10 | 10 | 10 |
| Ethanol (g) | 20 | 20 | 20 | 20 | 20 |
| Purified Water (g) | 40 | 40 | 40 | 40 | 40 |
| Ethanol Content after Drying (%) | 8.5 | 5.82 | 0.85 | 1.11 | 1.19 |

EXAMPLE 6

4 g of cyclosporin A and 2 g of Tyloxapol and 3 g of Poloxamer 407 as emulsifiers were dissolved in ethanol. 10 g of porous dextrin was added to the ethanolic solution, and the resultant was formulated into granule in conventional manner. The ethanol content in the granule was measured by HPLC, and the result is shown in Table 2 below.

EXAMPLE 7

The procedure of Example 6 was repeated except that the amounts of the cyclosporin A, Poloxamer 407, ethanol and the porous dextrin were varied as shown in Table 2 to obtain the composition of the present invention in granule. Its ethanol content was measured and the result is shown in Table 2 below.

TABLE 2

| Composition | Ex. 6 | Ex. 7 |
|---|---|---|
| Cyclosporin A (g) | 4 | 4 |
| Tyloxapol (g) | 2 | — |
| Poloxamer 407 (g) | 3 | 4 |
| Porous dextrin (g) | 10 | 10 |
| Ethanol (g) | 5 | 5 |
| Ethanol Content after Drying (%) | 0.01 | 0.03 |

Test 1. Dissolution Test (1)

The powders prepared in Examples 1–5 were filled into hard capsules, and then the capsules were tested under the following conditions. The results are shown in Table 3 below. As comparative samples, simple mixtures of cyclosporin A, an emulsifier and dextrin, and SANDIMMUN soft capsule were used.

Dissolution Test Condition:
  Test Solution: artificial gastric juice (Ph 1.2) 900 ml
  Temperature: 37°±0.5° C.
  Method: Paddle Method Comparative Samples:
  Comparative Sample 1:
  Cyclosporin A:Poloxamer 407:Porous dextrin=2:1:5
  Comparative Sample 2:
  Cyclosporin A:Poloxamer 407=2:1
  Comparative Sample 3:
  SANDIMMUN soft capsule

TABLE 3

| Time | Concentration (µg/ml) | | | | | | | |
|---|---|---|---|---|---|---|---|---|
| | Example | | | | | Comparative Example | | |
| (min) | 1 | 2 | 3 | 4 | 5 | 1 | 2 | 3 |
| 5 | 5.0 | 3.0 | 5.5 | 4.0 | 2.6 | 0.5 | 0.4 | 0.25 |
| 10 | 7.2 | 4.6 | 7.7 | 6.0 | 3.8 | 0.7 | 0.7 | 0.65 |
| 20 | 8.8 | 6.3 | 9.3 | 7.4 | 5.0 | 1.0 | 1.0 | 1.00 |
| 30 | 9.7 | 7.3 | 9.7 | 8.3 | 5.9 | 0.9 | 0.9 | 1.50 |
| 60 | 11.3 | 8.6 | 10.8 | 9.7 | 7.7 | 1.6 | 1.6 | 2.00 |
| 120 | 13.4 | 9.5 | 11.5 | 10.9 | 8.9 | 2.2 | 2.2 | 2.95 |

Test 2 Dissolution Test (2)

The granules prepared in Examples 6 and 7 were filled into hard capsules, and then the capsules were tested under the following conditions. The results are shown in Table 4 below. As comparative samples, simple mixtures of cyclosporin A, emulsifier and dextrin, and SANDIMMUN soft capsule were used.

Dissolution Test Condition:
  Test Solution: artificial gastric juice (pH 1.2) 900 ml
  Temperature: 37°±0.5° C.
  Method: Paddle Method Comparative Samples:
  Comparative Sample 1:
  Cyclosporin A:Poloxamer 407:Porous dextrin=2:1:5
  Comparative Sample 2:
  Cyclosporin A:Poloxamer 407:=2:1
  Comparative Sample 3:
  SANDIMMUN soft capsule

TABLE 4

| Time | Concentration (µg/ml) | | | | |
|---|---|---|---|---|---|
| | Example | | Comparative Example | | |
| (min) | 6 | 7 | 1 | 2 | 3 |
| 5 | 5.8 | 9.0 | 0.5 | 0.4 | 0.25 |
| 10 | 7.3 | 10.6 | 0.7 | 0.7 | 0.65 |
| 20 | 8.4 | 11.5 | 0.8 | 1.0 | 1.00 |
| 30 | 8.9 | 11.7 | 0.9 | 0.9 | 1.50 |
| 60 | 9.7 | 12.1 | 1.2 | 1.6 | 2.00 |
| 120 | 8.7 | 11.8 | 1.3 | 2.2 | 2.95 |

Test 3 Bioavailability Test

The granule prepared in Example 7 was filled into hard capsules, and then the capsules were tested. As comparative sample, SANDIMMUN soft capsules were used.

Each of the test capsules and comparative capsules was administered to Beagle Dogs (9–12 kg) orally at a dose of 10 mg/kg of cyclosporin A. The dogs were fasted from 16 hours before until 4 hours after the administration of the drugs except water. Blood samples were taken in each amount of 100µ at 0.25, 0.5, 0.75, 1, 1.5, 2, 3, 4, 5, 6, 8, 10, 12 and 24 hours after the administration. The blood concentration of the cyclosporin A was measured by using RIA (radioimmunoassay) kit, and the results were shown in FIG. 1.

As shown in FIG. 1, the composition prepared in accordance with the present invention has a maximum blood concentration ($C_{max}$) which is higher than the comparative sample by about 1.5 times and an area under the curve (AUC) greater than the comparative sample by about 1.3 times.

As it is clear from the above results, the composition of the present invention has a remarkably improved dissolution rate as well as superior bioavailability.

While the invention has been described in connection with the above specific embodiments, it should be recognized that various modifications and changes may be made within the scope of the invention as define by the claims that follow.

What is claimed is:

1. A composition comprising 1.0 to 40 wt. % of a cyclosporin A, 0.1 to 30 wt. % of an emulsifier, and 5 to 80 wt. % of a porous dextrin, based on the total weight of the composition.

2. The composition of claim 1, wherein said emulsifier is Tyloxapol, Poloxamer, or a mixture thereof.

3. A process for preparing a composition containing a cyclosporin A, which comprises the steps of dissolving the cyclosporin A in ethanol with an emulsifier, adding a porous dextrin thereto to form a mixture, and drying the mixture.

4. The process of claim 3, wherein said emulsifier is Tyloxapol, Poloxamer, or a mixture thereof.

5. The process of claim 3, wherein said emulsifier is added in an amount of 0.1 to 30 wt. % based on the total weight of the composition.

6. The process of claim 3, wherein said porous dextrin is added in an amount of 5 to 80 wt. % based on the total weight of the composition.

7. The process of claim 3, wherein said porous dextrin is added in the form of an aqueous solution thereof.

8. The process of claim 7, wherein the concentration of said porous dextrin in the aqueous solution ranges from 20 to 50%.

9. The process of claim 3, wherein said drying method is performed by spray drying or under a reduced pressure.

10. A pharmaceutical formulation comprising the composition of claim 1 and a pharmacologically acceptable carrier.

11. The formulation of claim 10, which is a hard capsule.

* * * * *